(12) United States Patent
Schaller et al.

(10) Patent No.: US 11,992,038 B2
(45) Date of Patent: May 28, 2024

(54) LIQUID NICOTINE FORMULATION COMPRISING PARTIALLY WATER-SOLUBLE SOLVENT

(71) Applicant: Philip Morris Products S.A., Neuchatel (CH)

(72) Inventors: Jean-Pierre Schaller, Neuchatel (CH); Aline Vuarnoz-Bize, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 487 days.

(21) Appl. No.: 17/419,374

(22) PCT Filed: Dec. 31, 2019

(86) PCT No.: PCT/EP2019/087196
§ 371 (c)(1),
(2) Date: Jun. 29, 2021

(87) PCT Pub. No.: WO2020/141178
PCT Pub. Date: Jul. 9, 2020

(65) Prior Publication Data
US 2022/0071269 A1    Mar. 10, 2022

(30) Foreign Application Priority Data

Dec. 31, 2018  (EP) .................................. 18215964
Dec. 31, 2018  (EP) .................................. 18215966
Dec. 31, 2018  (EP) .................................. 18215969
Dec. 31, 2018  (EP) .................................. 18215976
Dec. 31, 2018  (EP) .................................. 18215983

(51) Int. Cl.
| | |
|---|---|
| A24B 15/167 | (2020.01) |
| A24B 15/32 | (2006.01) |
| A24F 40/05 | (2020.01) |
| A24F 40/10 | (2020.01) |
| A24F 40/46 | (2020.01) |
| A61K 9/00 | (2006.01) |
| A61K 31/465 | (2006.01) |

(52) U.S. Cl.
CPC .......... *A24B 15/167* (2016.11); *A24B 15/32* (2013.01); *A24F 40/05* (2020.01); *A24F 40/10* (2020.01); *A24F 40/46* (2020.01); *A61K 9/0078* (2013.01); *A61K 31/465* (2013.01)

(58) Field of Classification Search
None
See application file for complete search history.

(56) References Cited

U.S. PATENT DOCUMENTS

| | | |
|---|---|---|
| 2006/0018840 A1 | 1/2006 | Lechuga-Ballesteros et al. |
| 2007/0060639 A1 | 3/2007 | Wermeling |
| 2009/0181080 A1 | 7/2009 | Kottayil et al. |
| 2012/0325228 A1 | 12/2012 | Williams |
| 2014/0345631 A1 | 11/2014 | Bowen et al. |
| 2015/0013695 A1 | 1/2015 | McNeal et al. |
| 2015/0114409 A1 | 4/2015 | Brammer et al. |
| 2015/0117841 A1 | 4/2015 | Brammer et al. |
| 2015/0117842 A1 | 4/2015 | Brammer et al. |
| 2016/0227839 A1 | 8/2016 | Zuber. et al. |
| 2016/0302471 A1 | 10/2016 | Bowen et al. |
| 2016/0366927 A1 | 12/2016 | Liu |
| 2016/0366928 A1 | 12/2016 | Liu |
| 2017/0079319 A1 | 3/2017 | Muhammed et al. |
| 2017/0086500 A1 | 3/2017 | Li et al. |
| 2017/0325494 A1 | 11/2017 | Cameron et al. |
| 2017/0348494 A1 | 12/2017 | Havercroft et al. |
| 2017/0367386 A1 | 12/2017 | McElvany et al. |
| 2018/0325164 A1 | 11/2018 | Tiley et al. |
| 2018/0352862 A1 | 12/2018 | Mironov et al. |
| 2019/0091420 A1 | 3/2019 | McNeal et al. |
| 2022/0071270 A1* | 3/2022 | Schaller .................. A24F 40/05 |

FOREIGN PATENT DOCUMENTS

| | | |
|---|---|---|
| CA | 3 003 056 A1 | 5/2017 |
| CN | 103598672 A | 2/2014 |
| CN | 104256885 A | 1/2015 |
| CN | 104473323 A | 4/2015 |
| CN | 106562469 A | 4/2017 |
| CN | 106714589 A | 5/2017 |

(Continued)

OTHER PUBLICATIONS

Combined Chinese Office Action and Search Report dated Jan. 28, 2023 in Chinese Patent Application No. 201980079569.2 (with English Translation of Office Action Only), 5 pages.
International Search Report and Written Opinion dated Apr. 17, 2020 in PCT/EP2019/087196 filed on Dec. 31, 2019.
Extended European Search Report dated Jul. 2, 2019 in European Patent Application No. 18215964.0, 9 pages.
Extended European Search Report dated Jul. 2, 2019 in European Patent Application No. 18215976.4, 6 pages.
Extended European Search Report dated Jul. 2, 2019 in European Patent Application No. 18215969.9, 6 pages.
"Rhythm, Hack Your Life" Retrieved from the Internet: http://www.usonicig.com/rhythm/index.html, 2018, 5 pages.
Jed E. Rose, et al., "The Sensory Impact of Nicotine on Noradrenergic and Dopaminergic Neurons of the Nicotine Reward—Addiction Neurocircuitry" Journal of Addiction Research & Therapy, vol. 7, Issue 2, 2016, pp. 1-7.
Karel Talavera, et al., "Nicotine Activates the Chemosensory Cation Channel TRPA1" Nature Neuroscience, vol. 12, No. 10, Oct. 2009, 1293-1299.

(Continued)

*Primary Examiner* — Tho D Ta
(74) *Attorney, Agent, or Firm* — Oblon, McClelland, Maier & Neustadt, L.L.P.

(57) ABSTRACT

A liquid nicotine formulation for an aerosol-generating system is provided, the liquid nicotine formulation including: water; and one or more partially water-soluble, water-immiscible solvents having a water solubility at 20° C. of between about 20 mg/ml and about 100 mg/ml, the liquid nicotine formulation having a water content of greater than or equal to about 5 percent by weight and a partially water-soluble, water-immiscible solvent content of between about 2 percent by weight and about 30 percent by weight. A cartridge for an aerosol-generating system, and an aerosol-generating system, are also provided.

14 Claims, No Drawings

(56) References Cited

FOREIGN PATENT DOCUMENTS

| | | |
|---|---|---|
| DE | 10 2011 114 094 A1 | 3/2013 |
| EP | 3 021 699 A2 | 5/2016 |
| GB | 2532062 A | 5/2016 |
| GB | 2542389 A | 3/2017 |
| JP | 2006-109784 A | 4/2006 |
| RU | 2 659 887 C2 | 7/2018 |
| WO | WO 2015/042589 A1 | 3/2015 |
| WO | WO 2015/057996 A1 | 4/2015 |
| WO | WO 2015/117243 A1 | 8/2015 |
| WO | WO 2015/166219 A1 | 11/2015 |
| WO | WO 2017/081480 A1 | 5/2017 |
| WO | WO 2018/064032 A1 | 4/2018 |
| WO | WO 2018/073261 A1 | 4/2018 |
| WO | WO 2019/219457 A1 | 11/2019 |
| WO | WO 2019/219865 A1 | 11/2019 |

OTHER PUBLICATIONS

Jeffrey I. Seeman, et al., "On the Deposition of Volatiles and Semivolatiles from Cigarette Smoke Aerosols: Relative Rates of Transfer of Nicotine and Ammonia from Particles to the Gas Phase" Chemical Research in Toxicology, vol. 17, No. 8, 2004, pp. 1020-1037.

Combined Russian Office Action and Search Report dated Apr. 14, 2023 in Russian Patent Application No. 2021120291 (with English translation), 19 pages.

Combined Chinese Office Action and Search Report dated Jun. 1, 2022 in Chinese Patent Application No. 201980079569.2 (with English translation), 21 pages.

European Office Action dated Jul. 20, 2023 in European Patent Application No. 19831771.1, 5 pages.

Japanese Office Action mailed on Jan. 4, 2024 issued in Japanese Patent Application No. 2021-538442 filed on Dec. 31, 2019, with English Translation, total 17 pages.

\* cited by examiner

LIQUID NICOTINE FORMULATION COMPRISING PARTIALLY WATER-SOLUBLE SOLVENT

The invention relates to a liquid nicotine formulation for use in an aerosol-generating system. The invention also relates to a cartridge for an aerosol-generating system comprising the liquid nicotine formulation and an aerosol-generating system comprising the liquid nicotine formulation and an atomiser configured to generate an aerosol from the liquid nicotine formulation.

Aerosol-generating systems for delivering nicotine to a user that comprise an atomiser configured to generate an inhalable aerosol from a liquid nicotine formulation are known. Some known aerosol-generating systems comprise a thermal atomiser such as an electric heater that is configured to heat and vaporise the liquid nicotine formulation to generate an aerosol. Other known aerosol-generating systems comprise a non-thermal atomiser that is configured to generate an aerosol from the liquid nicotine formulation using, for example, impinging jet, ultrasonic or vibrating mesh technologies. Typical liquid nicotine formulations for use in aerosol-generating systems comprise glycerine, propylene glycol and water as solvents.

In such aerosol-generating systems, pulmonary delivery of the inhalable aerosol generated from the liquid nicotine formulation is important for user palatability and satisfaction. Nicotine adsorption through the pulmonary alveoli is rapid and efficient. By contrast, nicotine adsorption in the upper airways is slower and less efficient. Nicotine adsorption in the upper airways may also undesirably be perceived by a user as having a sensorial harshness and induce mouth and throat irritation.

It would be desirable to provide a liquid nicotine formulation for use in an aerosol-generating system that that enables generation of an aerosol providing improved nicotine satisfaction to a user compared to typical liquid nicotine formulations. In particular, it would be desirable to provide a liquid nicotine formulation for use in an aerosol-generating system that enables generation of an aerosol having improved lung deposition characteristics and nicotine retention compared to aerosols generated from typical liquid nicotine formulations.

According to a first aspect of the invention there is provided a liquid nicotine formulation for use in an aerosol-generating system, the liquid nicotine formulation comprising: at least one of water and one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to the first aspect of the invention there is also provided a cartridge for use in an aerosol-generating system, the cartridge containing a liquid nicotine formulation comprising: at least one of water and one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to the first aspect of the invention there is further provided an aerosol-generating system comprising: a liquid nicotine formulation comprising: at least one of water and one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a second aspect of the invention there is provided a liquid nicotine formulation for use in an aerosol-generating system, the liquid nicotine formulation comprising: at least one of water and one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to the second aspect of the invention there is also provided a cartridge for use in an aerosol-generating system, the cartridge containing a liquid nicotine formulation comprising: at least one of water and one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to the second aspect of the invention there is further provided an aerosol-generating system comprising: a liquid nicotine formulation comprising: at least one of water and one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

As used herein with reference to the invention, the term "liquid nicotine formulation" describes a liquid formulation comprising nicotine.

As used herein with reference to the invention, the term "nicotine" describes nicotine, nicotine base or a nicotine salt. In embodiments in which the liquid nicotine formulation comprises a nicotine base or a nicotine salt, the amounts of nicotine recited herein are the amount of free base nicotine or amount of protonated nicotine, respectively.

As used herein with reference to the invention, the term "water-miscible solvent" describes a compound other than water or an organic acid that is liquid at 20° C. and mixes with water in all proportions to form a homogenous solution.

As used herein with reference to the first aspect of the invention, the term "partially water-soluble, water-immiscible solvent" describes a compound that is liquid at 20° C. and has a water solubility at 20° C. of between about 20 mg/ml and about 100 mg/ml.

As used herein with reference to the second aspect of the invention, the term "partially water-soluble, water-immiscible solvent" describes a compound that is liquid at 20° C. and has a partition coefficient (log P) at 20° C. of between about 0.05 and about 0.5.

Unless stated otherwise, water solubility values recited herein are the water solubility measured based on the preliminary test of OECD (1995), *Test No.* 105*: Water Solubility*, OECD Guidelines for the Testing of Chemicals, Section 1, OECD Publishing, Paris, https://doi.org/10.1787/9789264069589-en. In a stepwise procedure, increasing volumes of distilled water are added at 20° C. to 0.1 g of the sample (solid substances must be pulverized) in a 10 ml glass-stoppered measuring cylinder. However, when the substance is an acid, the sample is added to the distilled water in the first step. After each addition of an amount of water, the mixture is shaken for 10 minutes and is visually checked for any undissolved parts of the sample. If, after addition of 10 ml of water, the sample or parts of it remain undissolved, the experiment is continued in a 100 ml measuring cylinder. The approximate solubility is given in Table 1 below under that volume of water in which complete dissolution of the sample occurs.

When the solubility is low, a long time may be required to dissolve a substance and at least 24 hours should be allowed. If, after 24 hours, the substance is still not dissolved, the measuring cylinder is placed for at 40° C. in an ultrasound bath for 15 minutes and another 24 hours allowed (up to a maximum of 96 hours). If the substance is still not dissolved, the solubility is considered to be below the limit value or not soluble.

TABLE 1

| | ml of water in which 0.1 g of sample is soluble | | | | | | |
|---|---|---|---|---|---|---|---|
| | 0.1 | 0.5 | 1 | 2 | 10 | 100 | >100 |
| Approximate solubility (mg/ml) | >1000 | 1000 to 200 | 200 to 100 | 100 to 50 | 50 to 10 | 10 to 1 | <1 |

Unless stated otherwise, partition coefficient (log P) values recited herein are the octanol/water partition coefficient (log $P_{OW}$) measured in accordance with: OECD (1995), *Test No. 107: Partition Coefficient (n-octanol/water): Shake Flask Method*, OECD Guidelines for the Testing of Chemicals, Section 1, OECD Publishing, Paris, https://doi.org/10.1787/9789264069626-en (for values in the range log $P_{OW}$ between −2 and 4); OECD (2004), *Test No. 117: Partition Coefficient (n-octanol/water), HPLC Method*, OECD Guidelines for the Testing of Chemicals, Section 1, OECD Publishing, Paris, https://doi.org/10.1787/9789264069824-en (for values in the range log $P_{OW}$ between 0 and 6); and OECD (2006), *Test No. 123: Partition Coefficient (1-Octanol/Water): Slow-Stirring Method*, OECD Guidelines for the Testing of Chemicals, Section 1, OECD Publishing, Paris, https://doi.org/10.1787/9789264015845-en (for values in the range log $P_{OW}$ up to 8.2).

Inclusion of a combination of at least one of water and one or more water-miscible solvents and one or more partially water-soluble, water-immiscible solvents in the liquid nicotine formulation according to the invention advantageously enables generation of an inhalable aerosol providing improved nicotine satisfaction to a user compared to aerosols generated from typical liquid nicotine formulations. In particular, inclusion of a combination of at least one of water and one or more water-miscible solvents and one or more partially water-soluble, water-immiscible solvents in the liquid nicotine formulation according to the invention advantageously enables generation of an inhalable aerosol having improved lung deposition characteristics and nicotine retention compared to aerosols generated from typical liquid nicotine formulations.

Due to inclusion of a combination of at least one of water and one or more water-miscible solvents and one or more partially water-soluble, water-immiscible solvents, when used in an aerosol-generating system the liquid nicotine formulation according to the invention generates an inhalable aerosol comprising dual-phase particles or droplets comprising an aqueous or water-miscible phase and a water-immiscible phase. This advantageously reduces nicotine adsorption in the upper airways and enhances pulmonary nicotine delivery and retention. Without wishing to be bound by theory, the improvement in pulmonary nicotine delivery and retention is believed to be due to coating or enveloping of the aqueous or water-miscible phase by the water immiscible phase. This is believed to reduce nicotine evaporation and adsorption in the upper airways.

Unless stated otherwise, percentages by weight of components of the liquid nicotine formulation recited herein are based on the total weight of the liquid nicotine formulation.

The liquid nicotine formulation may comprise natural nicotine or synthetic nicotine.

The liquid nicotine formulation may have a nicotine content of greater than or equal to about 0.5 percent by weight.

Preferably, the liquid nicotine formulation has a nicotine content of greater than or equal to about 1 percent by weight. More preferably, the liquid nicotine formulation has a nicotine content of greater than or equal to about 1.5 percent by weight.

The liquid nicotine formulation may have a nicotine content of less than or equal to about 10 percent by weight. The liquid nicotine formulation may have a nicotine content of less than or equal to about 8 percent by weight.

Preferably, the liquid nicotine formulation has a nicotine content of less than or equal to about 5 percent by weight. More preferably, the liquid nicotine formulation has a nicotine content of less than or equal to about 3 percent by weight.

The liquid nicotine formulation may have a nicotine content of between about 0.5 percent by weight and about 10 percent by weight. For example, the liquid nicotine formulation may have a nicotine content of between about 0.5 percent by weight and about 8 percent by weight, between about 0.5 percent by weight and about 5 percent by weight or between about 0.5 percent by weight and about 3 percent by weight.

Preferably, the liquid nicotine formulation has a nicotine content of between about 1 percent by weight and about 10 percent by weight. For example, the liquid nicotine formulation may have a nicotine content of between about 1 percent by weight and about 8 percent by weight, between about 1 percent by weight and about 5 percent by weight or between about 1 percent by weight and about 3 percent by weight.

More preferably, the liquid nicotine formulation has a nicotine content of between about 1.5 percent by weight and about 10 percent by weight. For example, the liquid nicotine formulation may have a nicotine content of between about 1.5 percent by weight and about 8 percent by weight, between about 1.5 percent by weight and about 5 percent by weight or between about 1.5 percent by weight and about 3 percent by weight.

The liquid nicotine formulation comprises at least one of water and one or more water-miscible solvents. That is, the liquid nicotine comprises water or one or more miscible solvents or both water and one or more miscible solvents.

Preferably, the liquid nicotine formulation has a total water and water-miscible solvent content of greater than or equal to about 50 percent by weight or greater than or equal to about 55 percent by weight.

More preferably, the liquid nicotine formulation has a total water and water-miscible solvent content of greater than or equal to about 60 percent by weight. For example, the liquid nicotine formulation may have a total water and water-miscible solvent content of greater than or equal to about 65 percent by weight, greater than or equal to about 70 percent by weight, greater than or equal to about 75 percent by weight, greater than or equal to about 80 percent by weight or greater than or equal to about 85 percent by weight.

In embodiments in which the liquid nicotine formulation comprises water, the water may advantageously help to dissolve and stabilise polar components and ionic components of the liquid nicotine formulation.

In embodiments in which the liquid nicotine formulation comprises water, preferably the liquid nicotine formulation has a water content of greater than or equal to about 5 percent by weight. More preferably, the liquid nicotine formulation has a water-content of greater than or equal to about 10 percent by weight. For example, the liquid nicotine formulation may have a water content of greater than or equal to about 15 percent by weight, greater than or equal to about 20 percent by weight, greater than or equal to about 25 percent by weight, greater than or equal to about 30 percent by weight or greater than or equal to about 35 percent by weight.

In embodiments in which the liquid nicotine formulation comprises water, the liquid nicotine formulation may have a water content of less than or equal to about 90 percent by weight.

In embodiments in which the liquid nicotine formulation comprises water, preferably the liquid nicotine formulation has a water content of less than or equal to about 85 percent by weight. More preferably, the liquid nicotine formulation has a water content of less than or equal to about 80 percent by weight. For example, the liquid nicotine formulation may have a water content of less than or equal to about 75 percent by weight, less than or equal to about 70 percent by weight or less than or equal to about 65 percent by weight.

In embodiments in which the liquid nicotine formulation comprises water, the liquid nicotine formulation may have a water content of between about 5 percent by weight and about 90 percent by weight. Preferably the liquid nicotine formulation has a water content of between about 5 percent by weight and about 85 percent by weight. For example, the liquid nicotine formulation may have a water content of between about 5 percent by weight and about 80 percent by weight, between about 5 percent by weight and about 75 percent by weight, between about 5 percent by weight and about 70 percent by weight or between about 5 percent by weight and about 65 percent by weight.

The liquid nicotine formulation may have a water content of between about 10 percent by weight and about 90 percent by weight. More preferably, the liquid nicotine formulation has a water content of between about 10 percent by weight and about 85 percent by weight. For example, the liquid nicotine formulation may have a water content of between about 10 percent by weight and about 80 percent by weight, between about 10 percent by weight and about 75 percent by weight, between about 10 percent by weight and about 70 percent by weight or between about 10 percent by weight and about 65 percent by weight.

In embodiments in which the liquid nicotine formulation comprises water, the liquid nicotine formulation may have a water content of between about 15 percent by weight and about 90 percent by weight or between about 15 percent by weight and about 85 percent by weight. For example, the liquid nicotine formulation may have a water content of between about 15 percent by weight and about 80 percent by weight, between about 15 percent by weight and about 75 percent by weight, between about 15 percent by weight and about 70 percent by weight or between about 15 percent by weight and about 65 percent by weight.

The liquid nicotine formulation may have a water content of between about 20 percent by weight and about 90 percent by weight or between about 20 percent by weight and about 85 percent by weight. For example, the liquid nicotine formulation may have a water content of between about 20 percent by weight and about 80 percent by weight, between about 20 percent by weight and about 75 percent by weight, between about 20 percent by weight and about 70 percent by weight or between about 20 percent by weight and about 65 percent by weight.

The liquid nicotine formulation may have a water content of between about 25 percent by weight and about 90 percent by weight or between about 25 percent by weight and about 85 percent by weight. For example, the liquid nicotine formulation may have a water content of between about 25 percent by weight and about 80 percent by weight, between about 25 percent by weight and about 75 percent by weight, between about 25 percent by weight and about 70 percent by weight or between about 25 percent by weight and about 65 percent by weight.

The liquid nicotine formulation may have a water content of between about 30 percent by weight and about 90 percent by weight or between about 30 percent by weight and about 85 percent by weight. For example, the liquid nicotine formulation may have a water content of between about 30 percent by weight and about 80 percent by weight, between about 30 percent by weight and about 75 percent by weight, between about 30 percent by weight and about 70 percent by weight or between about 30 percent by weight and about 65 percent by weight.

The liquid nicotine formulation may have a water content of between about 35 percent by weight and about 90 percent by weight or between about 35 percent by weight and about 85 percent by weight. For example, the liquid nicotine formulation may have a water content of between about 35 percent by weight and about 80 percent by weight, between about 35 percent by weight and about 75 percent by weight, between about 35 percent by weight and about 70 percent by weight or between about 35 percent by weight and about 65 percent by weight.

In embodiments in which the liquid nicotine formulation comprises one or more water-miscible solvents, the one or more water-miscible solvents may advantageously help to dissolve and stabilise polar components and ionic components of the liquid nicotine formulation.

In embodiments in which the liquid nicotine formulation comprises one or more water-miscible solvents, preferably the liquid nicotine formulation has a water-miscible solvent content of greater than or equal to about 5 percent by weight. More preferably, the liquid nicotine formulation has a water-miscible solvent content of greater than or equal to about 10 percent by weight. For example, the liquid nicotine formulation may have a water-miscible solvent content of greater than or equal to about 15 percent by weight, greater than or equal to about 20 percent by weight or greater than or equal to about 25 percent by weight.

The liquid nicotine formulation may have a water-miscible solvent content of less than or equal to about 80 percent by weight or less than or equal to about 75 percent by weight.

In embodiments in which the liquid nicotine formulation comprises one or more water-miscible solvents, preferably the liquid nicotine formulation has a water-miscible solvent content of less than or equal to about 70 percent by weight. More preferably, the liquid nicotine formulation has a water-miscible solvent content of less than or equal to about 60 percent by weight. For example, the liquid nicotine formulation may have a water-miscible solvent content of less than or equal to about 50 percent by weight or less than or equal to about 40 percent by weight.

In embodiments in which the liquid nicotine formulation comprises one or more water-miscible solvents, preferably the liquid nicotine formulation has a water-miscible solvent content of between about 5 percent by weight and about 70 percent by weight. For example, the liquid nicotine formulation may have a water-miscible solvent content of between about 5 percent by weight and about 60 percent by weight, between about 5 percent by weight and about 50 percent by weight or between about 5 percent by weight and about 40 percent by weight.

More preferably, the liquid nicotine formulation has a water-miscible solvent content of between about 10 percent by weight and about 70 percent by weight. For example, the liquid nicotine formulation may have a water-miscible solvent content of between about 10 percent by weight and about 60 percent by weight, between about 10 percent by weight and about 50 percent by weight or between about 10 percent by weight and about 40 percent by weight.

In embodiments in which the liquid nicotine formulation comprises one or more water-miscible solvents, the liquid nicotine formulation may have a water-miscible solvent content of between about 15 percent by weight and about 70 percent by weight, between about 15 percent by weight and about 60 percent by weight, between about 15 percent by weight and about 50 percent by weight or between about 15 percent by weight and about 40 percent by weight.

The liquid nicotine formulation may have a water-miscible solvent content of between about 20 percent by weight and about 70 percent by weight, between about 20 percent by weight and about 60 percent by weight, between about 20 percent by weight and about 50 percent by weight or between about 20 percent by weight and about 40 percent by weight.

The liquid nicotine formulation may have a water-miscible solvent content of between about 25 percent by weight and about 70 percent by weight, between about 25 percent by weight and about 60 percent by weight, between about 25 percent by weight and about 50 percent by weight or between about 25 percent by weight and about 40 percent by weight.

In embodiments in which the liquid nicotine formulation comprises one or more water-miscible solvents, preferably, the one or more water-miscible solvents are one or more water-miscible polyhydric alcohols.

As used herein with reference to the invention, the term "water-miscible polyhydric alcohol" describes a polyhydric alcohol that is liquid at 20° C. and mixes with water in all proportions to form a homogenous solution.

According to a preferred embodiment of the first aspect of the invention there is provided a liquid nicotine formulation for use in an aerosol-generating system, the liquid nicotine formulation comprising: at least one of water and one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is also provided a cartridge for use in an aerosol-generating system, the cartridge containing a liquid nicotine formulation comprising: at least one of water and one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is further provided an aerosol-generating system comprising: a liquid nicotine formulation comprising: at least one of water and one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a preferred embodiment of the second aspect of the invention there is provided a liquid nicotine formulation for use in an aerosol-generating system, the liquid nicotine formulation comprising: at least one of water and one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is also provided a cartridge for use in an aerosol-generating system, the cartridge containing a liquid nicotine formulation comprising: at least one of water and one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is further provided an aerosol-generating system comprising: a liquid nicotine formulation comprising: at least one of water and one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

In embodiments in which the liquid nicotine formulation comprises one or more water-miscible polyhydric alcohols, preferably the liquid nicotine formulation has a water-miscible polyhydric alcohol content of greater than or equal to about 5 percent by weight. More preferably, the liquid nicotine formulation has a water-miscible polyhydric alcohol content of greater than or equal to about 10 percent by weight. For example, the liquid nicotine formulation may have a water-miscible polyhydric alcohol content of greater than or equal to about 15 percent by weight, greater than or equal to about 20 percent by weight or greater than or equal to about 25 percent by weight.

In embodiments in which the liquid nicotine formulation comprises one or more water-miscible polyhydric alcohols, the liquid nicotine formulation may have a water-miscible polyhydric alcohol content of less than or equal to about 80 percent by weight or less than or equal to about 75 percent by weight.

In embodiments in which the liquid nicotine formulation comprises one or more water-miscible polyhydric alcohols, preferably the liquid nicotine formulation has a water-miscible polyhydric alcohol content of less than or equal to about 70 percent by weight. More preferably, the liquid nicotine formulation has a water-miscible polyhydric alcohol content of less than or equal to about 60 percent by weight. For example, the liquid nicotine formulation may have a water-miscible polyhydric alcohol content of less than or equal to about 50 percent by weight or less than or equal to about 40 percent by weight.

In embodiments in which the liquid nicotine formulation comprises one or more water-miscible polyhydric alcohols, preferably the liquid nicotine formulation has a water-miscible polyhydric alcohol content of between about 5 percent by weight and about 70 percent by weight. For example, the liquid nicotine formulation may have a water-miscible polyhydric alcohol content of between about 5 percent by weight and about 60 percent by weight, between about 5 percent by weight and about 50 percent by weight or between about 5 percent by weight and about 40 percent by weight.

More preferably, the liquid nicotine formulation has a water-miscible polyhydric alcohol content of between about 10 percent by weight and about 70 percent by weight. For example, the liquid nicotine formulation may have a water-miscible polyhydric alcohol content of between about 10 percent by weight and about 60 percent by weight, between about 10 percent by weight and about 50 percent by weight or between about 10 percent by weight and about 40 percent by weight.

In embodiments in which the liquid nicotine formulation comprises one or more water-miscible polyhydric alcohols, the liquid nicotine formulation may have a water-miscible polyhydric alcohol content of between about 15 percent by weight and about 70 percent by weight, between about 15 percent by weight and about 60 percent by weight, between about 15 percent by weight and about 50 percent by weight or between about 15 percent by weight and about 40 percent by weight.

The liquid nicotine formulation may have a water-miscible polyhydric alcohol content of between about 20 percent by weight and about 70 percent by weight, between about 20 percent by weight and about 60 percent by weight, between about 20 percent by weight and about 50 percent by weight or between about 20 percent by weight and about 40 percent by weight.

The liquid nicotine formulation may have a water-miscible polyhydric alcohol content of between about 25 percent by weight and about 70 percent by weight, between about 25 percent by weight and about 60 percent by weight, between about 25 percent by weight and about 50 percent by weight or between about 25 percent by weight and about 40 percent by weight.

In embodiments in which the liquid nicotine formulation comprises one or more water-miscible polyhydric alcohols, preferably the one or more water-miscible polyhydric alcohols are selected from the group consisting of 1,3-butanediol, glycerine, propylene glycol, and triethylene glycol.

More preferably, the one or more water-miscible polyhydric alcohols are selected from the group consisting of glycerine and propylene glycol.

Most preferably, the one or more water-miscible polyhydric alcohols are selected from the group consisting of vegetable glycerine and propylene glycol.

According to a preferred embodiment of the first aspect of the invention there is provided a liquid nicotine formulation for use in an aerosol-generating system, the liquid nicotine formulation comprising: at least one of water and one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is also provided a cartridge for use in an aerosol-generating system, the cartridge containing a liquid nicotine formulation comprising: at least one of water and one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is further provided an aerosol-generating system comprising: a liquid nicotine formulation comprising: at least one of water and one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a preferred embodiment of the second aspect of the invention there is provided a liquid nicotine formulation for use in an aerosol-generating system, the liquid nicotine formulation comprising: at least one of water and one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is also provided a cartridge for use in an aerosol-generating system, the cartridge containing a liquid nicotine formulation comprising: at least one of water and one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is further provided an aerosol-generating system comprising: a liquid nicotine formulation comprising: at least one of water and one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

In embodiments in which the liquid nicotine formulation comprises one or more water-miscible polyhydric alcohols selected from the group consisting of glycerine and propylene glycol, the liquid nicotine formulation may have a combined glycerine and propylene glycol content of less than or equal to about 80 percent by weight or less than or equal to about 75 percent by weight.

In embodiments in which the liquid nicotine formulation comprises one or more water-miscible polyhydric alcohols selected from the group consisting of glycerine and propylene glycol, preferably the liquid nicotine formulation has a combined glycerine and propylene glycol content of less than or equal to about 70 percent by weight. More preferably, the liquid nicotine formulation has a combined glycerine and propylene glycol content of less than or equal to about 60 percent by weight. For example, the liquid nicotine formulation may have a combined glycerine and propylene glycol content of less than or equal to about 50 percent by weight or less than or equal to about 40 percent by weight.

In embodiments in which the liquid nicotine formulation comprises one or more water-miscible polyhydric alcohols selected from the group consisting of glycerine and propylene glycol, the liquid nicotine formulation may have a combined glycerine and propylene glycol content of between about 5 percent by weight and about 80 percent by weight or between about 5 percent by weight and about 75 percent by weight.

In embodiments in which the liquid nicotine formulation comprises one or more water-miscible polyhydric alcohols selected from the group consisting of glycerine and propylene glycol, preferably the liquid nicotine formulation has a combined glycerine and propylene glycol content of between about 5 percent by weight and about 70 percent by weight. For example, the liquid nicotine formulation may have a combined glycerine and propylene glycol content of between about 5 percent by weight and about 60 percent by weight, between about 5 percent by weight and about 50 percent by weight or between about 5 percent by weight and about 40 percent by weight.

In embodiments in which the liquid nicotine formulation comprises one or more water-miscible polyhydric alcohols selected from the group consisting of glycerine and propylene glycol, the liquid nicotine formulation may have a combined glycerine and propylene glycol content of between about 10 percent by weight and about 80 percent by weight or between about 10 percent by weight and about 75 percent by weight.

More preferably, the liquid nicotine formulation has a combined glycerine and propylene glycol content of between about 10 percent by weight and about 70 percent by weight. For example, the liquid nicotine formulation may have a combined glycerine and propylene glycol content of between about 10 percent by weight and about 60 percent by weight, between about 10 percent by weight and about 50 percent by weight or between about 10 percent by weight and about 40 percent by weight.

In embodiments in which the liquid nicotine formulation comprises one or more water-miscible polyhydric alcohols selected from the group consisting of glycerine and propylene glycol, the liquid nicotine formulation may have a combined glycerine and propylene glycol content of between about 15 percent by weight and about 80 percent by weight, between about 15 percent by weight and about 75 percent by weight, between about 15 percent by weight and about 70 percent by weight, between about 15 percent by weight and about 60 percent by weight, between about 15 percent by weight and about 50 percent by weight or between about 15 percent by weight and about 40 percent by weight.

The liquid nicotine formulation may have a combined glycerine and propylene glycol content of between about 20 percent by weight and about 80 percent by weight, between about 20 percent by weight and about 75 percent by weight, between about 20 percent by weight and about 70 percent by weight, between about 20 percent by weight and about 60 percent by weight, between about 20 percent by weight and about 50 percent by weight or between about 20 percent by weight and about 40 percent by weight.

The liquid nicotine formulation may have a combined glycerine and propylene glycol content of between about 25 percent by weight and about 80 percent by weight, between about 15 percent by weight and about 75 percent by weight, between about 25 percent by weight and about 70 percent by weight, between about 25 percent by weight and about 60 percent by weight, between about 25 percent by weight and about 50 percent by weight or between about 25 percent by weight and about 40 percent by weight.

Preferably, the liquid nicotine formulation comprises water and one or more water-miscible solvents.

According to a preferred embodiment of the first aspect of the invention there is provided a liquid nicotine formulation for use in an aerosol-generating system, the liquid nicotine formulation comprising: water; one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is also provided a cartridge for use in an aerosol-generating system, the cartridge containing a liquid nicotine formulation comprising: water; one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a preferred embodiment of the first aspect of the invention there is further provided an aerosol-generating system comprising: a liquid nicotine formulation comprising: water; one or more water-miscible solvents; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a preferred embodiment of the second aspect of the invention there is provided a liquid nicotine formulation for use in an aerosol-generating system, the liquid nicotine formulation comprising: water; one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is also provided a cartridge for use in an aerosol-generating system, the cartridge containing a liquid nicotine formulation comprising: water; one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a preferred embodiment of the second aspect of the invention there is further provided an aerosol-generating system comprising: a liquid nicotine formulation comprising: water; one or more water-miscible solvents; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

The liquid nicotine formulation may have a combined water and water-miscible solvent content of greater than or equal to about 50 percent by weight or greater than or equal to about 55 percent by weight. Preferably, the liquid nicotine formulation has a combined water and water-miscible solvent content of greater than or equal to about 60 percent by weight. More preferably, the liquid nicotine formulation has a combined water and water-miscible solvent content of greater than or equal to 65 percent by weight. For example, the liquid nicotine formulation may have a combined water and water-miscible solvent content of greater than or equal to about 70 percent by weight, greater than or equal to about 75 percent by weight, greater than or equal to about 80 percent by weight or greater than or equal to about 85 percent by weight.

More preferably, the liquid nicotine formulation comprises water and one or more water-miscible polyhydric alcohols.

According to a more preferred embodiment of the first aspect of the invention there is provided a liquid nicotine formulation for use in an aerosol-generating system, the liquid nicotine formulation comprising: water; one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a more preferred embodiment of the first aspect of the invention there is also provided a cartridge for use in an aerosol-generating system, the cartridge containing a liquid nicotine formulation comprising: water; one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a more preferred embodiment of the first aspect of the invention there is further provided an aerosol-generating system comprising: a liquid nicotine formulation comprising: water; one or more water-miscible polyhydric alcohols; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a more preferred embodiment of the second aspect of the invention there is provided a liquid nicotine formulation for use in an aerosol-generating system, the liquid nicotine formulation comprising: water; one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a more preferred embodiment of the second aspect of the invention there is also provided a cartridge for use in an aerosol-generating system, the cartridge containing a liquid nicotine formulation comprising: water; one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a more preferred embodiment of the second aspect of the invention there is further provided an aerosol-generating system comprising: a liquid nicotine formulation comprising: water; one or more water-miscible polyhydric alcohols; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

In embodiments in which the liquid nicotine formulation comprises water and one or more water-miscible polyhydric alcohols, the liquid nicotine formulation may have a combined water and water-miscible polyhydric alcohol content of greater than or equal to about 50 percent by weight or greater than or equal to about 55 percent by weight.

In embodiments in which the liquid nicotine formulation comprises water and one or more water-miscible polyhydric alcohols, preferably the liquid nicotine formulation has a combined water and water-miscible polyhydric alcohol content of greater than or equal to about 60 percent by weight. More preferably, the liquid nicotine formulation has a combined water and water-miscible polyhydric alcohol content of greater than or equal to 65 percent by weight. For example, the liquid nicotine formulation may have a combined water and water-miscible polyhydric alcohol content of greater than or equal to about 70 percent by weight, greater than or equal to about 75 percent by weight, greater than or equal to about 80 percent by weight or greater than or equal to about 85 percent by weight.

Most preferably, the liquid nicotine formulation comprises water and one or more water-miscible polyhydric alcohols selected from the group consisting of glycerine and propylene glycol.

According to a more preferred embodiment of the first aspect of the invention there is provided a liquid nicotine formulation for use in an aerosol-generating system, the liquid nicotine formulation comprising: water; one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a more preferred embodiment of the first aspect of the invention there is also provided a cartridge for use in an aerosol-generating system, the cartridge containing a liquid nicotine formulation comprising: water; one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight.

According to a more preferred embodiment of the first aspect of the invention there is further provided an aerosol-generating system comprising: a liquid nicotine formulation comprising: water; one or more water-miscible polyhydric alcohols selected from the group consisting of glycerine and propylene glycol; and one or more partially water-soluble, water-immiscible solvents having a water solubility at 20° C. of between about 20 mg/ml and about 100 mg/ml, wherein the liquid nicotine formulation has a partially water-soluble, water-immiscible solvent content of greater than or equal to about 2 percent by weight; and an atomiser configured to generate an aerosol from the liquid nicotine formulation.

According to a more preferred embodiment of the second aspect of the invention there is further provided an aerosol-generating system comprising: a liquid nicotine formulation comprising: water; one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a more preferred embodiment of the second aspect of the invention there is also provided a cartridge for use in an aerosol-generating system, the cartridge containing a liquid nicotine formulation comprising: water; one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight.

According to a more preferred embodiment of the second aspect of the invention there is further provided an aerosol-generating system comprising: a liquid nicotine formulation comprising: water; one or more water-miscible polyhydric alcohols selected from the group consisting of glycerine and propylene glycol; and one or more partially water-soluble, water-immiscible solvents having a partition coefficient (log P) at 20° C. of between about 0.05 and about 0.5, wherein the liquid nicotine formulation has a partially water-soluble, water-immiscible solvent content of greater than or equal to about 2 percent by weight; and an atomiser configured to generate an aerosol from the liquid nicotine formulation.

In embodiments in which the liquid nicotine formulation comprises water and one or more water-miscible polyhydric alcohols selected from the group consisting of glycerine and propylene glycol, the liquid nicotine formulation may have a combined water, glycerine and propylene glycol content of greater than or equal to about 50 percent by weight or greater than or equal to about 55 percent by weight.

In embodiments in which the liquid nicotine formulation comprises water and one or more water-miscible polyhydric alcohols selected from the group consisting of glycerine and propylene glycol, preferably the liquid nicotine formulation has a combined water, glycerine and propylene glycol content of greater than or equal to about 60 percent by weight. More preferably, the liquid nicotine formulation has a combined water, glycerine and propylene glycol content of greater than or equal to 65 percent by weight. For example, the liquid nicotine formulation may have a combined water, glycerine and propylene glycol content of greater than or equal to about 70 percent by weight, greater than or equal to about 75 percent by weight, greater than or equal to about 80 percent by weight or greater than or equal to about 85 percent by weight.

Preferably, the liquid nicotine formulation has a glycerine content of greater than or equal to about 5 percent by weight.

More preferably, the liquid nicotine formulation has a glycerine content of greater than or equal to about 6 percent by weight. For example, the liquid nicotine formulation may have a glycerine content of greater than or equal to about 7 percent by weight or greater than or equal to about 8 percent by weight.

The liquid nicotine formulation may have a glycerine content of less than or equal to about 80 percent by weight or less than or equal to about 75 percent by weight.

Preferably, the liquid nicotine formulation has a glycerine content of less than or equal to about 70 percent by weight. More preferably, the liquid nicotine formulation has a glycerine content of less than or equal to about 60 percent by weight. For example, the liquid nicotine formulation may have a glycerine content of less than or equal to about 50 percent by weight or less than or equal to about 40 percent by weight.

Preferably, the liquid nicotine formulation has a glycerine content of between about 5 percent by weight and about 70 percent by weight. For example, the liquid nicotine formulation may have a glycerine content of between about 5 percent by weight and about 60 percent by weight, between about 5 percent by weight and about 50 percent by weight or between about 5 percent by weight and about 40 percent by weight.

More preferably, the liquid nicotine formulation has a glycerine content of between about 6 percent by weight and about 70 percent by weight. For example, the liquid nicotine formulation may have a glycerine content of between about 6 percent by weight and about 60 percent by weight, between about 6 percent by weight and about 50 percent by weight or between about 6 percent by weight and about 40 percent by weight.

The liquid nicotine formulation may have a glycerine content of between about 7 percent by weight and about 70 percent by weight, between about 7 percent by weight and about 60 percent by weight, between about 7 percent by weight and about 50 percent by weight or between about 7 percent by weight and about 40 percent by weight.

The liquid nicotine formulation may have a glycerine content of between about 8 percent by weight and about 70 percent by weight, between about 8 percent by weight and about 60 percent by weight, between about 8 percent by weight and about 50 percent by weight or between about 8 percent by weight and about 40 percent by weight.

The liquid nicotine formulation comprises one or more water-immiscible solvents.

As used herein with reference to the first aspect of the invention, the term "water-immiscible solvent" describes a compound that is liquid at 20° C. and has a water solubility at 20° C. of less than or equal to about 100 mg/ml.

As used herein with reference to the second aspect of the invention, the term "water-immiscible solvent" describes a compound that is liquid at 20° C. and has a partition coefficient (log P) at 20° C. of greater than or equal to about 0.05.

According to the first aspect of the invention, the liquid nicotine formulation comprises one or more partially water-soluble, water-immiscible solvents having a water solubility at 20° C. of between about 20 mg/ml and about 100 mg/ml.

According to the second aspect of the invention, the liquid nicotine formulation comprises one or more partially water-soluble, water-immiscible solvents having a partition coefficient (log P) at 20° C. of between about 0.05 and about 0.5.

The one or more partially water-soluble, water-immiscible solvents may advantageously help to dissolve and stabilise non-polar components of the liquid nicotine formulation.

The one or more partially water-soluble, water-immiscible solvents may reduce the hygroscopicity of an aerosol generated from the liquid nicotine formulation when used in an aerosol-generating system. This may advantageously reduce or prevent increases in the particle or droplet size of the aerosol when inhaled by a user as a result of adsorption of water in the respiratory tract.

The liquid nicotine formulation has a partially water-soluble, water-immiscible solvent content of greater than or equal to about 2 percent by weight.

Preferably, the liquid nicotine formulation has a partially water-soluble, water-immiscible solvent content of greater than or equal to about 2.5 percent by weight.

For example, the liquid nicotine formulation may have a partially water-soluble, water-immiscible solvent content of greater than or equal to about 3 percent by weight, greater than or equal to about 4 percent by weight or greater than or equal to about 5 percent by weight, greater than or equal to about 6 percent by weight, greater than or equal to about 7 percent by weight or greater than or equal to about 8 percent by weight.

Preferably, the liquid nicotine formulation has a partially water-soluble, water-immiscible solvent content of less than or equal to about 30 percent by weight. For example, the liquid nicotine formulation may have a partially water-soluble, water-immiscible solvent content of less than or equal to about 25 percent by weight, less than or equal to about 20 percent by weight or less than or equal to about 15 percent by weight.

Preferably, the liquid nicotine formulation has a partially water-soluble, water-immiscible solvent content of between about 2 percent by weight and about 30 percent by weight. For example, the liquid nicotine formulation may have a partially water-soluble, water-immiscible solvent content of between about 2 percent by weight and about 25 percent by weight, between about 2 percent by weight and about 20 percent by weight or between about 2 percent by weight and about 15 percent by weight.

More preferably, the liquid nicotine formulation has a partially water-soluble, water-immiscible solvent content of between about 2.5 percent by weight and about 30 percent by weight. For example, the liquid nicotine formulation may have a partially water-soluble, water-immiscible solvent content of between about 2.5 percent by weight and about 25 percent by weight, between about 2.5 percent by weight and about 20 percent by weight or between about 2.5 percent by weight and about 15 percent by weight.

The liquid nicotine formulation may have a partially water-soluble, water-immiscible solvent content of between about 3 percent by weight and about 30 percent by weight. For example, the liquid nicotine formulation may have a partially water-soluble, water-immiscible solvent content of between about 3 percent by weight and about 25 percent by weight, between about 3 percent by weight and about 20 percent by weight or between about 3 percent by weight and about 15 percent by weight.

The liquid nicotine formulation may have a partially water-soluble, water-immiscible solvent content of between about 4 percent by weight and about 30 percent by weight. For example, the liquid nicotine formulation may have a partially water-soluble, water-immiscible solvent content of between about 4 percent by weight and about 25 percent by weight, between about 4 percent by weight and about 20 percent by weight or between about 4 percent by weight and about 15 percent by weight.

The liquid nicotine formulation may have a partially water-soluble, water-immiscible solvent content of between about 5 percent by weight and about 30 percent by weight. For example, the liquid nicotine formulation may have a partially water-soluble, water-immiscible solvent content of between about 5 percent by weight and about 25 percent by weight, between about 5 percent by weight and about 20 percent by weight or between about 5 percent by weight and about 15 percent by weight.

The liquid nicotine formulation may have a partially water-soluble, water-immiscible solvent content of between about 6 percent by weight and about 30 percent by weight. For example, the liquid nicotine formulation may have a partially water-soluble, water-immiscible solvent content of between about 6 percent by weight and about 25 percent by weight, between about 6 percent by weight and about 20 percent by weight or between about 6 percent by weight and about 15 percent by weight.

The liquid nicotine formulation may have a partially water-soluble, water-immiscible solvent content of between about 7 percent by weight and about 30 percent by weight. For example, the liquid nicotine formulation may have a partially water-soluble, water-immiscible solvent content of between about 7 percent by weight and about 25 percent by weight, between about 7 percent by weight and about 20 percent by weight or between about 7 percent by weight and about 15 percent by weight.

The liquid nicotine formulation may have a partially water-soluble, water-immiscible solvent content of between about 8 percent by weight and about 30 percent by weight. For example, the liquid nicotine formulation may have a partially water-soluble, water-immiscible solvent content of between about 8 percent by weight and about 25 percent by weight, between about 8 percent by weight and about 20 percent by weight or between about 8 percent by weight and about 15 percent by weight.

The ratio of the weight percent partially water-soluble, water-immiscible solvent content to the weight percent nicotine content of the liquid nicotine formulation may be greater than or equal to about 0.75.

That is, the weight percent partially water-soluble, water-immiscible solvent content of the liquid nicotine formulation may be at least about 0.75 times the weight percent nicotine content of the liquid nicotine formulation.

Preferably, the ratio of the weight percent partially water-soluble, water-immiscible solvent content to the weight percent nicotine content of the liquid nicotine formulation is greater than or equal to about 1. For example, the ratio of the weight percent partially water-soluble, water-immiscible solvent content to the weight percent nicotine content of the liquid nicotine formulation may be greater than or equal to about 1.25, greater than or equal to about 1.5 or greater than or equal to about 1.75.

The ratio of the weight percent partially water-soluble, water-immiscible solvent content to the weight percent nicotine content of the liquid nicotine formulation may be less than or equal to about 20.

That is, the weight percent partially water-soluble, water-immiscible solvent content of the liquid nicotine formulation may be less than or equal to 20 times the weight percent nicotine content of the liquid nicotine formulation.

Preferably, the ratio of the weight percent partially water-soluble, water-immiscible solvent content to the weight percent nicotine content of the liquid nicotine formulation is less than or equal to about 18. For example, the ratio of the weight percent partially water-soluble, water-immiscible solvent content to the weight percent nicotine content of the liquid nicotine formulation may be less than or equal to about 16, less than or equal to about 14 or less than or equal to about 12.

The ratio of the weight percent partially water-soluble, water-immiscible solvent content to the weight percent nicotine content of the liquid nicotine formulation may be between about 0.75 and about 20, between about 0.75 and about 18, between about 0.75 and about 16, between about 0.75 and about 14 or between about 0.75 and about 12.

Preferably, the ratio of the weight percent partially water-soluble, water-immiscible solvent content to the weight percent nicotine content of the liquid nicotine formulation is between about 1 and about 20, between about 1 and about 18, between about 1 and about 16, between about 1 and about 14 or between about 1 and about 12.

The ratio of the weight percent partially water-soluble, water-immiscible solvent content to the weight percent nicotine content of the liquid nicotine formulation may be between about 1.25 and about 20, between about 1.25 and about 18, between about 1.25 and about 16, between about 1.25 and about 14 or between about 1.25 and about 12.

The ratio of the weight percent partially water-soluble, water-immiscible solvent content to the weight percent nicotine content of the liquid nicotine formulation may be between about 1.5 and about 20, between about 1.5 and about 18, between about 1.5 and about 16, between about 1.5 and about 14 or between about 1.5 and about 12.

The ratio of the weight percent partially water-soluble, water-immiscible solvent content to the weight percent nicotine content of the liquid nicotine formulation may be between about 1.75 and about 20, between about 1.75 and about 18, between about 1.75 and about 16, between about 1.75 and about 14 or between about 1.75 and about 12.

The ratio of the weight percent partially water-soluble, water-immiscible solvent content to the weight percent water-miscible solvent content of the liquid nicotine formulation may be greater than or equal to about 0.06.

That is, the weight percent partially water-soluble, water-immiscible solvent content of the liquid nicotine formulation may be at least about 0.06 times the weight percent water-miscible solvent content of the liquid nicotine formulation.

Preferably, the ratio of the weight percent partially water-soluble, water-immiscible solvent content to the weight percent water-miscible solvent content of the liquid nicotine formulation is greater than or equal to about 0.08. For example, the ratio of the weight percent partially water-soluble, water-immiscible solvent content to the weight percent water-miscible solvent content of the liquid nicotine formulation may be greater than or equal to about 0.1, greater than or equal to about 0.12 or greater than or equal to about 0.14.

The ratio of the weight percent partially water-soluble, water-immiscible solvent content to the weight percent water-miscible solvent content of the liquid nicotine formulation may be less than or equal to about 1.2.

That is, the weight percent partially water-soluble, water-immiscible solvent content of the liquid nicotine formulation may be less than or equal to about 1.2 times the weight percent water-miscible solvent content of the liquid nicotine formulation.

Preferably, the ratio of the weight percent partially water-soluble, water-immiscible solvent content to the weight percent water-miscible solvent content of the liquid nicotine formulation is less than or equal to about 1. For example, the ratio of the weight percent partially water-soluble, water-immiscible solvent content to the weight percent water-miscible solvent content of the liquid nicotine formulation may be less than or equal to about 0.8, less than or equal to about 0.6 or less than or equal to about 0.4.

The ratio of the weight percent partially water-soluble, water-immiscible solvent content to the weight percent water-miscible solvent content of the liquid nicotine formulation may be between about 0.06 and about 1.2, between about 0.06 and about 1, between about 0.06 and about 0.8, between about 0.06 and about 0.6 or between about 0.06 and about 0.4.

Preferably, the ratio of the weight percent partially water-soluble, water-immiscible solvent content to the weight percent water-miscible solvent content of the liquid nicotine formulation is between about 0.08 and about 1.2, between about 0.08 and about 1, between about 0.08 and about 0.8, between about 0.08 and about 0.6 or between about 0.08 and about 0.4.

The ratio of the weight percent partially water-soluble, water-immiscible solvent content to the weight percent water-miscible solvent content of the liquid nicotine formulation may be between about 0.1 and about 1.2, between about 0.1 and about 1, between about 0.1 and about 0.8, between about 0.1 and about 0.6 or between about 0.1 and about 0.4.

The ratio of the weight percent partially water-soluble, water-immiscible solvent content to the weight percent water-miscible solvent content of the liquid nicotine formulation may be between about 0.12 and about 1.2, between about 0.12 and about 1, between about 0.12 and about 0.8, between about 0.1 and about 0.6 or between about 0.12 and about 0.4.

The ratio of the weight percent partially water-soluble, water-immiscible solvent content to the weight percent water-miscible solvent content of the liquid nicotine formulation may be between about 0.14 and about 1.2, between about 0.14 and about 1, between about 0.14 and about 0.8, between about 0.14 and about 0.6 or between about 0.14 and about 0.4.

The ratio of the weight percent partially water-soluble, water-immiscible solvent content to the weight percent water content of the liquid nicotine formulation may be greater than or equal to about 0.025.

That is, the weight percent partially water-soluble, water-immiscible solvent content of the liquid nicotine formulation may be at least about 0.02 times the weight percent water content of the liquid nicotine formulation.

Preferably, the ratio of the weight percent partially water-soluble, water-immiscible solvent content to the weight percent water content of the liquid nicotine formulation is greater than or equal to about 0.03. For example, the ratio of the weight percent partially water-soluble, water-immiscible solvent content to the weight percent water content of the liquid nicotine formulation may be greater than or equal to about 0.05, greater than or equal to about 0.075 or greater than or equal to about 0.1.

The ratio of the weight percent partially water-soluble, water-immiscible solvent content to the weight percent water content of the liquid nicotine formulation may be less than or equal to about 5.

That is, the weight percent partially water-soluble, water-immiscible solvent content of the liquid nicotine formulation may be less than or equal to about 5 times the weight percent water content of the liquid nicotine formulation.

Preferably, the ratio of the weight percent partially water-soluble, water-immiscible solvent content to the weight percent water content of the liquid nicotine formulation is less than or equal to about 1. For example, the ratio of the weight percent partially water-soluble, water-immiscible solvent content to the weight percent water content of the liquid nicotine formulation may be less than or equal to about 0.8, less than or equal to about 0.6 or less than or equal to about 0.4.

The ratio of the weight percent partially water-soluble, water-immiscible solvent content to the weight percent water content of the liquid nicotine formulation may be between about 0.02 and about 1.2, between about 0.02 and about 1, between about 0.02 and about 0.8, between about 0.02 and about 0.6 or between about 0.02 and about 0.4.

Preferably, the ratio of the weight percent partially water-soluble, water-immiscible solvent content to the weight percent water content of the liquid nicotine formulation is between about 0.03 and about 1.2, between about 0.03 and about 1, between about 0.03 and about 0.8, between about 0.03 and about 0.6 or between about 0.03 and about 0.4.

The ratio of the weight percent partially water-soluble, water-immiscible solvent content to the weight percent water content of the liquid nicotine formulation may be between about 0.05 and about 1.2, between about 0.05 and about 1, between about 0.05 and about 0.8, between about 0.05 and about 0.6 or between about 0.05 and about 0.4.

The ratio of the weight percent partially water-soluble, water-immiscible solvent content to the weight percent water content of the liquid nicotine formulation may be between about 0.75 and about 1.2, between about 0.75 and about 1, between about 0.75 and about 0.8, between about 0.75 and about 0.6 or between about 0.75 and about 0.4.

The ratio of the weight percent partially water-soluble, water-immiscible solvent content to the weight percent water content of the liquid nicotine formulation may be between about 0.1 and about 1.2, between about 0.1 and about 1, between about 0.1 and about 0.8, between about 0.1 and about 0.6 or between about 0.1 and about 0.4.

The one or more partially water-soluble, water-immiscible solvents may have a maximum carbon chain length of less than or equal to 12. For example, the one or more partially water-soluble, water-immiscible solvents may have a maximum carbon chain length of less than or equal to 10.

Preferably, the one or more partially water-soluble, water-immiscible solvents are selected from the group consisting of polysorbate 80, triethyl citrate and triacetin.

More preferably, the one or more partially water-soluble, water-immiscible solvents are selected from the group consisting of triethyl citrate and triacetin.

The liquid nicotine formulation may comprise one or more water-insoluble, water-immiscible solvents.

As used herein with reference to the first aspect of the invention, the term "water-insoluble, water-immiscible solvent" describes a compound that is liquid at 20° C. and has a water solubility at 20° C. of less than or equal to about 5 mg/ml.

As used herein with reference to the second aspect of the invention, the term "water-insoluble, water-immiscible solvent" describes a compound that is liquid at 20° C. and has a partition coefficient (log P) at 20° C. of greater than about 5.

The liquid nicotine formulation may have a water-insoluble, water-immiscible solvent content of greater than or equal to about 0.5 percent by weight or greater than or equal to about 1 percent by weight. For example, the liquid nicotine formulation may have a water-insoluble, water-immiscible solvent content of greater than or equal to about 2 percent by weight, greater than or equal to about 3 percent by weight, greater than or equal to about 4 percent by weight or greater than or equal to about 6 percent by weight.

The liquid nicotine formulation may have a water-insoluble, water-immiscible solvent content of less than or equal to about 30 percent by weight or less than or equal to about 25 percent by weight. For example, the liquid nicotine formulation may have a water-insoluble, water-immiscible solvent content of less than or equal to about 20 percent by weight, less than or equal to about 15 percent by weight or less than or equal to about 10 percent by weight.

The liquid nicotine formulation may have a water-insoluble, water-immiscible solvent content of between about 0.5 percent by weight and about 30 percent by weight or between about 0.5 percent by weight and about 25 percent by weight. For example, the liquid nicotine formulation may have a water-insoluble, water-immiscible solvent content of between about 0.5 percent by weight and about 20 percent by weight, between about 0.5 percent by weight and about 15 percent by weight or between about 0.5 percent by weight and about 10 percent by weight.

The liquid nicotine formulation may have a water-insoluble, water-immiscible solvent content of between about 1 percent by weight and about 30 percent by weight or between about 1 percent by weight and about 25 percent by weight. For example, the liquid nicotine formulation may have a water-insoluble, water-immiscible solvent content of between about 1 percent by weight and about 20 percent by weight, between about 1 percent by weight and about 15 percent by weight or between about 1 percent by weight and about 10 percent by weight.

The liquid nicotine formulation may have a water-insoluble, water-immiscible solvent content of between about 2 percent by weight and about 30 percent by weight or between about 2 percent by weight and about 25 percent by weight. For example, the liquid nicotine formulation may have a water-insoluble, water-immiscible solvent content of between about 2 percent by weight and about 20 percent by weight, between about 2 percent by weight and about 15 percent by weight or between about 2 percent by weight and about 10 percent by weight.

The liquid nicotine formulation may have a water-insoluble, water-immiscible solvent content of between about 3 percent by weight and about 30 percent by weight or between about 3 percent by weight and about 25 percent by weight. For example, the liquid nicotine formulation may have a water-insoluble, water-immiscible solvent content of between about 3 percent by weight and about 20 percent by weight, between about 3 percent by weight and about 15 percent by weight or between about 3 percent by weight and about 10 percent by weight.

The liquid nicotine formulation may have a water-insoluble, water-immiscible solvent content of between about 4 percent by weight and about 30 percent by weight or between about 4 percent by weight and about 25 percent by weight. For example, the liquid nicotine formulation may have a water-insoluble, water-immiscible solvent content of between about 4 percent by weight and about 20 percent by weight, between about 4 percent by weight and about 15 percent by weight or between about 4 percent by weight and about 10 percent by weight.

The liquid nicotine formulation may have a water-insoluble, water-immiscible solvent content of between about 6 percent by weight and about 30 percent by weight or between about 6 percent by weight and about 25 percent by weight. For example, the liquid nicotine formulation may have a water-insoluble, water-immiscible solvent content of between about 6 percent by weight and about 20 percent by weight, between about 6 percent by weight and about 15 percent by weight or between about 6 percent by weight and about 10 percent by weight.

The one or more water-insoluble, water-immiscible solvents may have a maximum carbon chain length of less than or equal to 30. For example, the one or more water-insoluble, water-immiscible solvents may have a maximum carbon chain length of less than or equal to 20, less than or equal to 18, less than or equal to 16, less than or equal to 14 or less than or equal to 12.

Suitable water-insoluble, water-immiscible solvents include, but are not limited to oleic acid and MIGLYOL® (mixture of decanoyl- and octanoyl glycerides).

The ratio of the weight percent partially water-soluble, water-immiscible solvent content to the weight percent water-insoluble, water-immiscible solvent content of the liquid nicotine formulation may be greater than or equal to about 0.2.

That is, the weight percent partially water-soluble, water-immiscible solvent content of the liquid nicotine formulation may be at least about 0.2 times the weight percent water-insoluble, water-immiscible solvent content of the liquid nicotine formulation.

Preferably, the ratio of the weight percent partially water-soluble, water-immiscible solvent content to the weight percent water-insoluble, water-immiscible solvent content of the liquid nicotine formulation is greater than or equal to about 0.4. For example, the ratio of the weight percent partially water-soluble, water-immiscible solvent content to the weight percent water-insoluble, water-immiscible solvent content of the liquid nicotine formulation may be greater than or equal to about 0.6, greater than or equal to about 0.8 or greater than or equal to about 1.

The ratio of the weight percent partially water-soluble, water-immiscible solvent content to the weight percent water-insoluble, water-immiscible solvent content of the liquid nicotine formulation may be less than or equal to about 35.

That is, the weight percent partially water-soluble, water-immiscible solvent content of the liquid nicotine formulation may be less than or equal to 35 times the weight percent water-insoluble, water-immiscible solvent content of the liquid nicotine formulation.

Preferably, the ratio of the weight percent partially water-soluble, water-immiscible solvent content to the weight percent water-insoluble, water-immiscible solvent content of the liquid nicotine formulation is less than or equal to about 30. For example, the ratio of the weight percent partially water-soluble, water-immiscible solvent content to the weight percent water-insoluble, water-immiscible solvent content of the liquid nicotine formulation may be less than or equal to about 25, less than or equal to about 20 or less than or equal to about 15.

The ratio of the weight percent partially water-soluble, water-immiscible solvent content to the weight percent water-insoluble, water-immiscible solvent content of the liquid nicotine formulation may be between about 0.2 and about 35, between about 0.2 and about 30, between about 0.2 and about 25, between about 0.2 and about 20 or between about 0.2 and about 15.

Preferably, the ratio of the weight percent partially water-soluble, water-immiscible solvent content to the weight percent water-insoluble, water-immiscible solvent content of the liquid nicotine formulation is between about 0.4 and about 35, between about 0.4 and about 30, between about 0.4 and about 25, between about 0.4 and about 20 or between about 0.4 and about 15.

The ratio of the weight percent partially water-soluble, water-immiscible solvent content to the weight percent water-insoluble, water-immiscible solvent content of the liquid nicotine formulation may be between about 0.6 and about 35, between about 0.6 and about 30, between about 0.6 and about 25, between about 0.6 and about 20 or between about 0.6 and about 15.

The ratio of the weight percent partially water-soluble, water-immiscible solvent content to the weight percent water-insoluble, water-immiscible solvent content of the liquid nicotine formulation may be between about 0.8 and about 35, between about 0.8 and about 30, between about 0.8 and about 25, between about 0.8 and about 20 or between about 0.8 and about 15.

The liquid nicotine formulation may be a substantially uncaffeinated liquid nicotine formulation.

As used herein with reference to the invention, the term "substantially uncaffeinated liquid nicotine formulation" describes a liquid nicotine formulation having a caffeine content of less than 0.5 percent by weight. For example, the liquid nicotine formulation may have a caffeine content of less than about 0.4 percent by weight, less than about 0.3 percent by weight or less than about 0.2 percent by weight.

The liquid nicotine formulation may be a substantially caffeine-free liquid nicotine formulation.

As used herein with reference to the invention, the term "substantially caffeine-free liquid nicotine formulation" describes a liquid nicotine formulation having a caffeine content of less than about 0.1 percent by weight.

The liquid nicotine formulation may be a caffeine-free liquid nicotine formulation.

As used herein with reference to the invention, the term "caffeine-free liquid nicotine formulation" describes a liquid nicotine formulation having a caffeine content of 0 percent by weight.

As used herein with reference to the invention, the term "caffeine" describes caffeine or a caffeine salt. When referring to a caffeine salt, the amounts of caffeine recited herein are the amount of caffeine cation.

The liquid nicotine formulation may comprise one or more solid emulsifiers.

As used herein with reference to the invention, the term "solid emulsifier" describes an emulsifier that is solid at 20° C. Suitable solid emulsifiers include, but are not limited to, 1-Stearoyl-rac-glycerol, Kolliphor® P 188, sodium caseinate, sodium dodecanoate and sodium docusate.

Preferably, the liquid nicotine formulation has a solid emulsifier content of less than or equal to about 8 percent by weight. More preferably, the liquid nicotine formulation has a solid emulsifier content of less than or equal to about 5 percent by weight.

Preferably, the liquid nicotine formulation comprises one or more water-soluble organic acids.

As used herein with reference to the invention, the term "water-soluble organic acid" describes an organic acid having a water solubility at 20° C. of greater than or equal to about 500 mg/ml.

The one or more water-soluble organic acids may advantageously bind nicotine in the liquid nicotine formulation through formation of one or nicotine salts.

The one or more nicotine salts may advantageously be dissolved and stabilised in the at least one of water and one or more water-miscible solvents. This may advantageously reduce nicotine adsorption in the upper airways and enhance pulmonary nicotine delivery and retention as discussed above.

More preferably, the liquid nicotine formulation comprises one or more water-soluble carboxylic acids.

Suitable water-soluble carboxylic acids include, but are not limited to, acetic acid, citric acid, lactic acid, levulinic acid, malic acid, malonic acid and pyruvic acid.

Most preferably, the liquid nicotine formulation comprises lactic acid.

Preferably, the liquid nicotine formulation has a water-soluble organic acid content of greater than or equal to about 2 percent by weight. More preferably, the liquid nicotine formulation has a water-soluble organic acid content of greater than or equal to about 3 percent by weight.

Preferably, the liquid nicotine formulation has a water-soluble organic acid content of less than or equal to about 8 percent by weight. More preferably, the liquid nicotine formulation has a water-soluble organic acid content of less than or equal to about 6 percent by weight.

Preferably, the liquid nicotine formulation has a water-soluble organic acid content of between about 2 percent by weight and about 8 percent by weight. For example, the liquid nicotine formulation may have a water-soluble organic acid content of between about 2 percent by weight and about 6 percent by weight.

More preferably, the liquid nicotine formulation has a water-soluble organic acid content of between about 3 percent by weight and about 8 percent by weight. For example, the liquid nicotine formulation may have a water-soluble organic acid content of between about 2 percent by weight and about 6 percent by weight.

The liquid nicotine formulation may comprise one or more flavourants. Suitable flavourants include, but are not limited to, menthol.

Preferably, the liquid nicotine formulation has a flavourant content of less than or equal to about 4 percent by weight. More preferably, the liquid nicotine formulation has a flavourant content of less than or equal to about 3 percent by weight.

According to the invention there is also provided a cartridge for use in an aerosol-generating system, the cartridge containing a liquid nicotine formulation according to the invention.

The cartridge may comprise an atomiser configured to generate an aerosol from the liquid nicotine formulation.

A cartridge containing the liquid nicotine formulation and an atomiser configured to generate an aerosol from the liquid nicotine formulation may be referred to as a "cartomiser".

The atomiser may be a thermal atomiser.

As used herein with reference to the invention, the term "thermal atomiser" describes an atomiser that is configured to heat the liquid nicotine formulation to generate an aerosol.

The cartridge may comprise any suitable type of thermal atomiser.

The thermal atomiser may comprise a heater and a liquid transport element configured to transport liquid nicotine formulation to the heater.

The liquid transport element may comprise a capillary wick. The heater may comprise a heater coil.

The thermal atomiser may comprise an electric heater. For example, the thermal atomiser may comprise an electric heater comprising a resistive heating element or an inductive heating element.

The atomiser may be a non-thermal atomiser.

As used herein with reference to the invention, the term "non-thermal atomiser" describes an atomiser that is configured to generate an aerosol from the liquid nicotine formulation by means other than heating.

The cartridge may comprise any suitable type of non-thermal atomiser.

For example, the non-thermal atomiser may be an impinging jet atomiser, an ultrasonic atomiser or a vibrating mesh atomiser.

According to the invention there is further provided an aerosol-generating system comprising a liquid nicotine formulation according to the invention and an atomiser configured to generate an aerosol from the liquid nicotine formulation.

The atomiser may be a thermal atomiser.

The aerosol-generating system may comprise any suitable type of thermal atomiser.

The thermal atomiser may comprise a heater and a liquid transport element configured to transport liquid nicotine formulation to the heater.

The liquid transport element may comprise a capillary wick. The heater may comprise a heater coil.

The thermal atomiser may comprise an electric heater. For example, the thermal atomiser may comprise an electric heater comprising a resistive heating element or an inductive heating element.

The atomiser may be a non-thermal atomiser.

The aerosol-generating system may comprise any suitable type of non-thermal atomiser.

For example, the non-thermal atomiser may be an impinging jet atomiser, an ultrasonic atomiser or a vibrating mesh atomiser.

The aerosol-generating system may comprise: a cartridge according to the invention containing the liquid nicotine formulation; and an aerosol-generating device comprising a housing defining a device cavity configured to receive at least a portion of the cartridge.

The aerosol-generating system may comprise: a consumable cartridge according to the invention containing the liquid nicotine formulation; and a reusable aerosol-generating device comprising a housing defining a device cavity configured to receive at least a portion of the cartridge.

The aerosol-generating device may comprise a battery and control electronics.

The aerosol-generating system may comprise: a cartridge according to the invention containing the liquid nicotine formulation and the atomiser; and an aerosol-generating device comprising a housing defining a device cavity configured to receive at least a portion of the cartridge.

The aerosol-generating system may comprise: a cartridge according to the invention containing the liquid nicotine formulation; and an aerosol-generating device comprising a housing defining a device cavity configured to receive at least a portion of the cartridge and the atomiser.

For the avoidance of doubt, features described above in relation to one aspect of the invention may also be applicable to other aspects of the invention. In particular, features described above in relation to the liquid nicotine formulation of the invention may also relate, where appropriate, to the cartridge of the invention and the aerosol-generating system of the invention. Similarly, features described above in relation to the cartridge of the invention may also relate, where appropriate, to the aerosol-generating system of the invention, and vice versa.

Embodiments of the invention will now be described, by way of example only, with reference to the following examples:

EXAMPLES 1-3

Three liquid nicotine formulations according to the invention (Examples 1, 2 and 3) were prepared having the compositions shown in Tables 2, 3 and 4.

TABLE 2

| Example 1 | | |
|---|---|---|
| Component | | % by weight |
| Nicotine | | 5 |
| Water | | 7 |
| Vegetable Glycerine | water-miscible solvent | 24 |
| Propylene Glycol | | 24 |
| Triethyl Citrate | partially water-soluble, water-immiscible solvent | 30 |
| Polysorbate 80 | | 1 |
| Lactic Acid | water-soluble organic acid | 7 |
| Flavourant | | 2 |

TABLE 3

| Example 2 | | |
|---|---|---|
| Component | | % by weight |
| Nicotine | | 2 |
| Water | | 31 |
| Vegetable Glycerine | water-miscible solvent | 31 |
| Triethyl Citrate | partially water-soluble, water-immiscible solvent | 30 |
| Polysorbate 80 | | 1 |
| Lactic Acid | water-soluble organic acid | 3 |
| Flavourant | | 2 |

TABLE 4

| Example 3 | | |
|---|---|---|
| Component | | % by weight |
| Nicotine | | 5 |
| Water | | 7 |
| Vegetable Glycerine | water-miscible solvent | 24 |
| Propylene Glycol | | 24 |
| Triacetin | partially water-soluble, water-immiscible solvent | 30 |
| Polysorbate 80 | | 1 |

TABLE 4-continued

| Example 3 | | |
|---|---|---|
| Component | | % by weight |
| Lactic Acid | water-soluble organic acid | 7 |
| Flavourant | | 2 |

EXAMPLES A-F

Six liquid nicotine formulations according to the invention (Examples A, B, C, D, E and F) were prepared having the compositions shown in Table 5. For comparison, two liquid nicotine formulations not according to the invention (Examples G and H) were also prepared having the composition shown in Table 5.

The liquid nicotine formulations of Examples A-H were each loaded into a cartridge for a Solaris e-cigarette. The nicotine retention of the aerosols generated when using the cartridges in a Solaris e-cigarette were measured using denuder tube technology essentially as described in Seeman, J. I.; Lipowicz, P. J.; Piadé, J.-J.; Poget, L.; Sanders, E. B.; Snyder, J. P.; Trowbridge, C. G., On the Deposition of Volatiles and Semivolatiles from Cigarette Smoke Aerosols: Relative Rates of Transfer of Nicotine and Ammonia from Particles to the Gas Phase. *Chemical Research in Toxicology* 2004, 17, 1020-1037, with the following modifications: the aerosol was pulled and not pushed; 55 ml puffs were used rather than 35 ml puffs; the denuder used was a 30 m Tygon® tube; the difference in nicotine yield was measured by comparing what was collected from the product onto a Cambridge pad with and without the Tygon® tube rather than by measuring what was collected by the denuder and by the Cambridge pad positioned after the denuder. For comparison, the nicotine retention of the smoke generated when combusting a conventional cigarette (Example I) was also measured. The results are shown in Table 5.

As shown in Table 5, the aerosols generated from the liquid nicotine formulations according to the invention (Examples A-F) provide nicotine retentions of greater than 40 percent. By contrast, the aerosols generated from the liquid formulations not according to the invention (Examples G and H) provide lower nicotine retentions of less than 30 percent.

The nicotine retention properties of the aerosols generated from the liquid nicotine formulations according to the invention (Examples A-F) are at least 13.5 times greater than the liquid formulation not according to the invention that does not comprise either a partially water-soluble, water-immiscible solvent having a water solubility at 20° C. of between about 20 mg/ml and about 100 mg/ml or a water-soluble organic acid (Example G).

The nicotine retention properties of the aerosols generated from the liquid nicotine formulations according to the invention (Examples A-F) are at least about 1.5 times greater than the liquid formulation not according to the invention that comprises an water-soluble organic acid, but does not comprise a partially water-soluble, water-immiscible solvent having a water solubility at 20° C. of between about 20 mg/ml and about 100 mg/ml (Example H).

The nicotine retention properties of the aerosols generated from the liquid nicotine formulations according to the invention (Examples A-F), which comprise a partially water-soluble, water-immiscible solvent having a water solubility at 20° C. of between about 20 mg/ml and about 100 mg/ml, are similar to the nicotine retention properties of the smoke generated from the conventional cigarette (Example I).

TABLE 5

| | | Example | | | | | | | | |
|---|---|---|---|---|---|---|---|---|---|---|
| | | A | B | C | D | E | F | G | H | I |
| Nicotine (% by weight) | | 2.7 | 2.7 | 2.7 | 2.7 | 2.7 | 2.7 | 5 | 5 | — |
| Water (% by weight) | | 80 | 60 | 40 | 80 | 60 | 40 | 20 | 20 | — |
| Vegetable Glycerine (% by weight) | water-miscible solvent | 8.7 | 25 | 45 | 8.7 | 25 | 45 | 37.5 | 34.7 | — |
| Propylene Glycol (% by weight) | | 1.5 | 4.2 | 4.2 | 1.5 | 4.2 | 4.2 | 37.5 | 34.7 | — |
| Triacetin (% by weight) | partially water-soluble, | 0.9 | 2 | 2 | 0.9 | 2 | 2 | 0 | 0 | — |
| Triethyl Citrate (% by weight) | water-immiscible solvent | 2 | 2 | 2 | 2 | 2 | 2 | 0 | 0 | — |
| Lactic Acid (% by weight) | water-soluble | 4.3 | 4.3 | 4.3 | 0 | 0 | 0 | 0 | 5.6 | — |
| Levulinic (% by weight) | organic acid | 0 | 0 | 0 | 4.3 | 4.3 | 4.3 | 0 | 0 | — |
| Nicotine Retention (%) | | 73.7 | 62.9 | 50.7 | 61.0 | 53.5 | 41.6 | 1-3% | 25-28% | 36-39% |

The invention claimed is:

1. A liquid nicotine formulation for an aerosol-generating system, the liquid nicotine formulation comprising:
   water; and
   one or more partially water-soluble, water-immiscible solvents having a water solubility at 20° C. of between about 20 mg/ml and about 100 mg/ml,
   wherein the liquid nicotine formulation has a water content of greater than or equal to about 5 percent by weight and a partially water-soluble, water-immiscible solvent content of between about 2 percent by weight and about 30 percent by weight.

2. The liquid nicotine formulation according to claim 1, further comprising one or more water-insoluble, water-immiscible solvents having a water solubility at 20° C. of less than or equal to about 5 mg/ml.

3. The liquid nicotine formulation according to claim 1, wherein the liquid nicotine formulation has a partially water-soluble, water-immiscible solvent content of greater than or equal to about 2.5 percent by weight.

4. The liquid nicotine formulation according to claim 1, wherein the one or more partially water-soluble, water-immiscible solvents are selected from the group consisting of triacetin and triethyl citrate.

5. The liquid nicotine formulation according to claim 1, further comprising one or more solid emulsifiers.

6. The liquid nicotine formulation according to claim 1, further comprising one or more water-soluble organic acids,
   wherein the liquid nicotine formulation has a water-soluble organic acid content of greater than or equal to about 2 percent by weight.

7. An aerosol-generating system, comprising:
   a liquid nicotine formulation according to claim 1; and
   an atomiser configured to generate an aerosol from the liquid nicotine formulation.

8. The liquid nicotine formulation according to claim 1, further comprising water and one or more water-miscible solvents.

9. The liquid nicotine formulation according to claim 8, wherein the liquid nicotine formulation has a total water and water-miscible solvent content of greater than or equal to about 60 percent by weight.

10. The liquid nicotine formulation according to claim 8, wherein the one or more water-miscible solvents are one or more water-miscible polyhydric alcohols selected from the group consisting of 1,3-butanediol, glycerine, propylene glycol, and triethylene glycol.

11. A cartridge for an aerosol-generating system, the cartridge containing a liquid nicotine formulation according to claim 1.

12. The cartridge according to claim 11, further comprising an atomiser configured to generate an aerosol from the liquid nicotine formulation.

13. A liquid nicotine formulation for an aerosol-generating system, the liquid nicotine formulation comprising:
   water; and
   one or more partially water-soluble, water-immiscible solvents having a partition coefficient (log P) at 20° C. of between about 0.05 and about 0.5,
   wherein the liquid nicotine formulation has a water content of greater than or equal to about 5 percent by weight and a partially water-soluble, water-immiscible solvent content of between about 2 percent by weight and about 30 percent by weight.

14. The liquid nicotine formulation according to claim 13, further comprising one or more water-insoluble, water-immiscible solvents having a partition coefficient (log P) at 20° C. of greater than about 5.

* * * * *